United States Patent
Golz-Berner et al.

(10) Patent No.: US 7,144,853 B2
(45) Date of Patent: Dec. 5, 2006

(54) ALCOHOL BASE MIXTURE FOR PERFUMED PREPARATIONS

(75) Inventors: Karin Golz-Berner, Monaco (MC); Leonhard Zastrow, Monaco (MC); Olivier Doucet, Villefranche s/Mer (FR)

(73) Assignee: Coty B.V., Haarlem (NL)

( * ) Notice: Subject to any disclaimer, the term of this patent is extended or adjusted under 35 U.S.C. 154(b) by 103 days.

(21) Appl. No.: 10/344,841

(22) PCT Filed: Aug. 14, 2001

(86) PCT No.: PCT/DE01/03070

§ 371 (c)(1),
(2), (4) Date: Feb. 13, 2003

(87) PCT Pub. No.: WO02/13769

PCT Pub. Date: Feb. 21, 2002

(65) Prior Publication Data

US 2003/0166500 A1    Sep. 4, 2003

(30) Foreign Application Priority Data

Aug. 15, 2000 (DE) ................................ 100 42 575

(51) Int. Cl.
*C11B 9/00* (2006.01)
(52) U.S. Cl. ........................................................... 512/1
(58) Field of Classification Search ..................... 512/1
See application file for complete search history.

(56) References Cited

FOREIGN PATENT DOCUMENTS

| DE | 199 41 819 | * | 3/2001 |
| EP | 0 875 236 | * | 11/1986 |
| EP | 1 106 174 | * | 6/2001 |

* cited by examiner

*Primary Examiner*—Monique T. Cole
(74) *Attorney, Agent, or Firm*—Akerman Senterfitt; Stephan A. Pendorf

(57) ABSTRACT

The invention relates to an alcoholic base mixture that contains extracts from fruit and dairy products. The mixture consists of the extract form pineapple fruit obtained by alcoholic extraction in the temperature range of from 10 to 30° C. and of the extract from yogurt obtained by alcoholic extraction in the temperature range of 10 to 30° C. The ratio of pineapple extract to yogurt extract ranges from 20:80 to 80:20. Used as a cosmetic perfumed preparation, for example as a perfume, the base mixture may generate a feeling of happiness by increasing the serotonin level, which effect is intensified by an additional bright yellow coloration.

7 Claims, No Drawings

ALCOHOL BASE MIXTURE FOR PERFUMED PREPARATIONS

CROSS REFERENCE TO RELATED APPLICATION

This application is a national stage of PCT/DE01/03070 filed Aug. 14, 2001 and based upon DE 100 42 575.5 filed Aug. 15, 2000 under the International Convention.

BACKGROUND OF THE INVENTION

1. Field of the Invention

The invention relates to an alcoholic base mixture that contains extracts from fruit and dairy products.

2. Description of the Related Art

A number of proposals have already been made for incorporating fruit or fruit extracts, including maritime plants and algae, into cosmetic products (DE-C-3515231 hafnia extract; DE-A-19824727 catechin and green tea).

It is also known to integrate milk or suitably prepared dairy products into cosmetic products. EP-A-839519, for example, discloses a cosmetic composition containing proteins and vitamins which contains 5–90% by weight of mammalian milk, 1–6% by weight of protein and yeast glucan.

SUMMARY OF THE INVENTION

The object of the present invention is to provide a base mixture for perfumed preparations which has special effects exerted via the skin.

DETAILED DESCRIPTION OF THE INVENTION

According to the invention, an alcoholic base mixture for perfumed preparations is provided, which base mixture is characterized in that it consists of the extract from pineapple fruit obtained by alcoholic extraction in the temperature range from 10 to 30° C. and of the extract from yogurt obtained by alcoholic extraction in the temperature range from 10 to 30° C., the ratio of pineapple extract to yogurt extract ranging from 20:80 to 80:20 relative to their weight.

A preferred ratio of the two extracts is in the range from 40:60 to 60:40.

The extract from pineapple fruit is obtained by means of an alcoholic extraction at a temperature ranging from 10 to 30° C., preferably from 15 to 25° C. The extraction process is based on fresh fruit which is cut into pieces and brought into contact with alcohol, e.g. ethyl alcohol, during a period of 5 to 36 hours while continuously being moved. Subsequently, the extract is filtered in order to separate any solid matter contained therein.

Due to the intensive extraction process, a number of alcohol soluble active agents are dissolved, but not the enzymes contained in the pineapple fruit. Part of the folic acid contained also passes into the extract.

As a second component, pure natural yogurt made from the milk of cows, sheep, goats or other animals or from a mixture of several kinds of milk is also subjected to an alcoholic extraction process, e.g. using ethyl alcohol, which takes place at a temperature ranging from 10 to 30° C., preferably from 15 to 25° C., and continues for a period of 5 to 36 hours during which the mixture is thoroughly moved. Subsequently, the liquid alcoholic phase is separated completely from the remaining matter, e.g. by means of several filtration processes. The extract which has thus been filtered is then sterilized. The active agents contained in the extract, e.g. vitamins, are preserved for further use. The alcoholic yogurt extract and the alcoholic pineapple extract, both of which have the form of a clear solution, are mixed with each other.

The alcoholic extracts serve as a basis for perfumed preparations such as perfumes, sprays, perfumed oils and possibly perfumed candles. Perfumes are particularly preferred. In addition to the aromatic components normally contained in perfumes, a perfume of the aforesaid kind, i.e. according to the invention, contains 0.5 to 10% by weight of the inventive mixture containing unusual active agents of pineapple fruit and yogurt.

The aforesaid active agents become effective once they have been applied on to the skin. The main special effect is a feeling of happiness which develops depending on the amount applied or the size of the body surface on to which the preparation is to be applied. The aforesaid feeling is not merely a feeling of happiness in the narrow sense, but a well balanced contentment, a feeling of relaxation coupled with pleasant sensations. The absorption of the product via the skin seems to have an effect on the serotonin level and the production of noradrenaline though there is no theory which proves this relationship.

The bright yellow coloration which is possible due to the pineapple extract can be intensified by adding yellow colourants to the cosmetic end product, e.g. a perfume. It is known that yellow colour can also stimulate feelings of happiness thus contributing to the overall effect of a perfume and, in particular, intensifying the feeling of well being experienced by the user.

The perfumed preparation containing the mixture according to the invention can contain carrier substances such as alcohols, oils, esters, propellants.

The invention will hereinafter be explained in more detail by means of examples. All quantities are in % by weight if not indicated otherwise.

EXAMPLE 1

Perfume

| | |
|---|---|
| Perfume oil | 13 |
| Ethanol | ad 100 |
| Base mixture containing pineapple extract: | |
| yogurt extract in a ratio of 55:45 | 2 |
| Yellow colourant | 0.1 |

The aforesaid components are mixed with each other by stirring. Subsequently, the mixture is left to mature and filtered.

EXAMPLE 2

The base mixture is produced by mixing approximately equal parts by weight of alcohol and fresh pineapple fruit which has been peeled and cut into pieces. The mixing process is continued during a period of 18 hours at a temperature of 20° C. Subsequently, the mixture is filtered and the filtrate is used as a starting component for the base mixture.

Further, 60 parts by weight of ethyl alcohol and 40 parts by weight of a fresh natural yogurt made from cow's milk are mixed with each other by stirring thoroughly during a period of 20 hours at a temperature of 20° C. and the mixture is subsequently filtered. The filtrate is filtered at least two more times and is finally passed through a Millipore filter.

The two extracts, both of which now have the form of a clear solution, are mixed with each other in the desired ratio and form the base mixture.

The invention claimed is:

1. An alcoholic base mixture for perfumed preparations which comprises:
   the extract from pineapple fruit obtained by alcoholic extraction in the temperature range from 10 to 30° C. and the extract from yogurt obtained by alcoholic extraction in the temperature range from 10 to 30° C., both fractions containing alcohol, the ratio of pineapple extract to yogurt extract ranging from 20:80 to 80:20.

2. A mixture according to claim 1 wherein the alcohol content of the mixture consists of ethyl alcohol.

3. A mixture according to claim 1 wherein the ratio of the two extracts is in the range from 40:60 to 60:40.

4. A mixture according to claim 1 wherein the said mixture is contained in a perfumed preparation in an amount ranging from 0.5 to 10% by weight relative to the total weight of the preparation.

5. A mixture according to claim 1 wherein the perfumed preparation is a perfume, a spray or a perfumed oil, particularly a perfume.

6. A mixture according to claim 1 wherein the perfumed preparation contains carrier substances such as alcohols, oils, esters, propellants.

7. A mixture according to claim 1 wherein the perfumed preparation has a bright yellow coloration.

* * * * *